US00PP23024P2

(12) United States Plant Patent
Pavlich

(10) Patent No.: US PP23,024 P2
(45) Date of Patent: Sep. 11, 2012

(54) ***CISTUS* PLANT NAMED 'MICKIE'**

(50) Latin Name: *Cistus×hybridus*
Varietal Denomination: Mickie

(76) Inventor: John C. Pavlich, East Olympia, WA (US)

( * ) Notice: Subject to any disclaimer, the term of this patent is extended or adjusted under 35 U.S.C. 154(b) by 0 days.

(21) Appl. No.: 13/200,295

(22) Filed: Sep. 21, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — June Hwu
*Assistant Examiner* — Louanne Krawczewicz Myers
(74) *Attorney, Agent, or Firm* — Klarquist Sparkman, LLP

(57) ABSTRACT

A new and distinct form of *Cistus* plant characterized by gold leaves with green centers, very stable leaf variegation, a low, mounding habit, and excellent vigor.

1 Drawing Sheet

Botanical denomination: *Cistus×hybridus*.
Variety designation: 'Mickie'.

BACKGROUND OF THE INVENTION

The present invention relates to a new and distinct cultivar of *Cistus×hybridus*, given the name, 'Mickie'. *Cistus* is in the family *Cistaceae*. This gold edged, green centered variegation was found as a branch mutation of *Cistus×hybridus* growing on a street planting in a commercial area in Woodinville, Wash.

Compared to the parent, *Cistus×hybridus*, an unpatented plant, the new cultivar is variegated and has shorter, darker inflorescences with a darker green flowering stem and a lower denser habit.

Compared to *Cistus×hybridus* 'Gold Prize', an unpatented plant, the new cultivar has a lower mounding habit and has stable variegation.

Compared to *Cistus* plant named 'Rencis', U.S. Plant Pat. No. 20,410, the new cultivar has a lower habit.

SUMMARY OF THE INVENTION

*Cistus* 'Mickie' is uniquely distinguished by:
1. gold leaves with green centers,
2. very stable leaf variegation,
3. a low, mounding habit, and
4. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of a two year old *Cistus* 'Mickie' with a flower growing in a five gallon container in June in Canby, Oreg.

FIG. 2 shows a four year old *Cistus* 'Mickie' growing in the garden in September in Canby, Oreg.

DETAILED PLANT DESCRIPTION

The following is a detailed description of the new *Cistus* cultivar based on observations of a two-year-old specimen grown outside in five gallon containers in Canby, Oreg. in mid June. The color descriptions are all based on The Royal Horticultural Society Colour Chart, 5$^{th}$ edition.

Plant:
- *Type*.—Evergreen shrub.
- *Form*.—Low, mounding.
- *Cold hardiness*.—USDA Zone 7-10.
- *Size*.—Grows to 81 cm wide and 28 cm high.
- *Vigor*.—Excellent.
- *Stem*.—Grows to 59 cm long and 6 mm wide, woody, with internodes 2 to 4 cm long, Brown 200A.
- *Rooting*.—Plants root easily from soft wood cuttings.

Leaf:
- *Type*.—Simple.
- *Arrangement*.—Opposite.
- *Shape*.—Ovate.
- *Venation*.—Pinnate.
- *Margins*.—Slightly undulate, entire.
- *Apex*.—Acute.
- *Base*.—Truncate.
- *Blade size*.—Grows to 4.7 cm long and 2.2 cm wide.
- *Surface texture*.—Rugose, pubescent on both sides.
- *Petiole*.—Grows to 15 mm long and 1 mm wide, pubescent, Yellow Green 146C with slight tints of Greyed Purple 187B on top side.
- *Fragrance*.—No unusual scent.
- *Leaf color*.—Brightest when grown in a full day of summer sun, topside Yellow 11A with centers irregularly blotched Yellow Green 147B, bottom side Yellow Green N144A with blotch Yellow Green 147B; older leaves, top side Yellow Green 147B with margins Yellow 11B, bottom side Yellow Green 147B with margins Yellow Green 146B. The fall foliage coloration is the same as the plant is an evergreen.

Inflorescence:

*Type*.—Usually two, cymose, at axillary nodes on branch tips.

*Peduncle*.—Grows to 5.5 cm long and 1 mm wide, pubescent, Yellow Green 144A.

*Pedicel*.—About 9 mm long and 1 mm wide, pubescent, Yellow Green 144A.

*Bloom period*.—June in Canby, Oreg.

Flower bud:

*Size*.—12 mm long and 5 mm wide at the widest point prior to opening.

*Description*.—Ovoid.

*Surface texture*.—Pubescent.

*Color*.—Yellow Green 145D strongly tinted Greyed Purple 187B.

Flower:

*Type*.—Actinomorphic.

*Shape*.—Rotate, cup shaped.

*Size*.—Grows to 35 mm wide and 6 mm deep.

*Corolla description*.—5 petals, each 2 cm long and 17 mm wide, flabellate in shape, margin entire, tip premorse to retuse, base cuneate, both sides glabrous and White NN155A with Yellow 12A at the very base.

*Calyx description*.—15 mm wide and 7 mm deep, with 5 sepals, grow to 9 mm long and 5 mm wide, ovate tips acuminate, margin entire, base attenuate, pubescent outside, glabrous inside, both sides Yellow 11D with edges Greyed Purple 187B.

*Pistil description*.—1, 3 mm long and 2 mm wide, ovary 1 mm long and 2 mm wide, pubescent and Yellow Green 145B; style less than 1 mm long, Yellow Green 145B, stigma globose, 2 mm long and 2 mm wide, Yellow 11D.

*Stamen description*.—About 80 in number and showy, filaments 3.5 mm long and Yellow 13A, anthers less than 1 mm long and Yellow Orange 23A, pollen Yellow Orange 23A.

*Fragrance*.—Slight.

*Lastingness*.—A flower lasts about 1 day.

Fruit and seed: None, sterile.

Pests and diseases: No particular pest or disease problems or resistance has been observed.

I claim:

1. A new and distinct form of *Cistus* plant as shown and described.

* * * * *

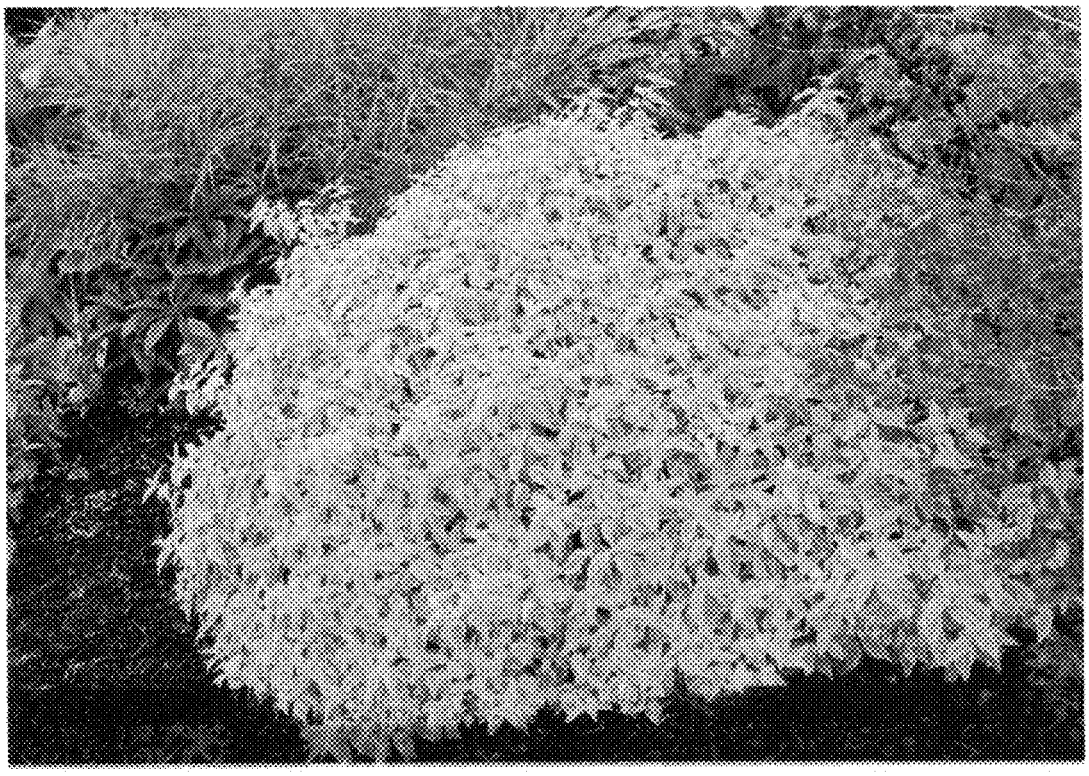

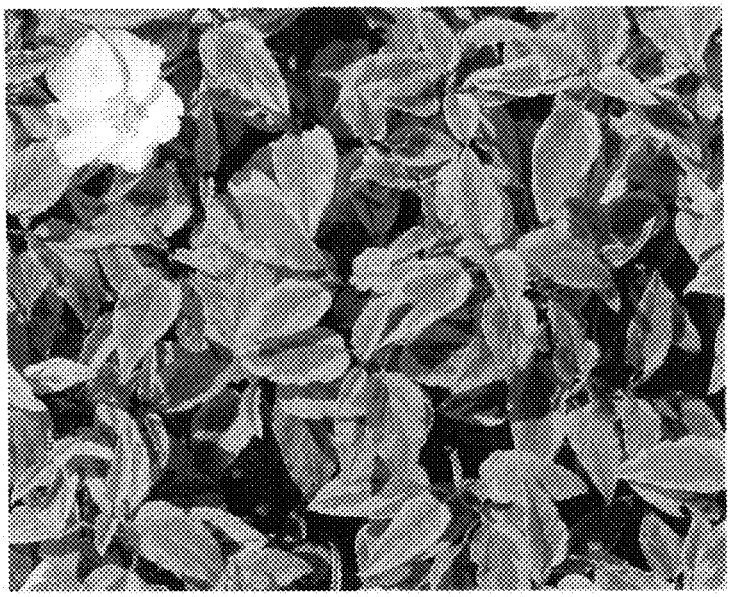
FIG. 1 above, FIG. 2 below